United States Patent [19]

Delpy et al.

[11] Patent Number: 4,957,000
[45] Date of Patent: Sep. 18, 1990

[54] APPARATUS FOR OBTAINING INFORMATION ON THE INTERIOR OF AN OBJECT

[75] Inventors: David T. Delpy; Hideo Hiruma; Susumu Suzuki, all of Shizuoka, Japan

[73] Assignee: Hamamatsu Photonics Kabushiki Kaisha, Shizuoka, Japan

[21] Appl. No.: 298,138

[22] Filed: Jan. 18, 1989

[30] Foreign Application Priority Data

Jan. 19, 1988 [JP] Japan ................................. 63-009007

[51] Int. Cl.⁵ ............................................ G01N 29/00
[52] U.S. Cl. .................................... 73/622; 128/653 R
[58] Field of Search ................. 73/622, 599, 600, 611, 73/628, 641, 626; 356/446; 128/660.01, 653 R

[56] References Cited

U.S. PATENT DOCUMENTS 2,549,836  4/1951  McIntyre et al. .................... 128/644
4,074,564  2/1978  Anderson et al. ..................... 73/596
4,458,689  7/1984  Surenson et al. .................... 128/660
4,489,729  12/1984 Sorenson et al. .................... 128/660

FOREIGN PATENT DOCUMENTS 62-124443  6/1987  Japan .

Primary Examiner—Jerry W. Myracle
Attorney, Agent, or Firm—Finnegan, Henderson, Farabow, Garrett, and Dunner

[57] ABSTRACT

An apparatus for obtaining information on the interior of an object, comprising irradiating elements for applying an electromagnetic wave or ultrasonic wave to an object being measured, detecting elements for detecting the electromagnetic wave or ultrasonic wave passed through and scattered inside the object, a holder for supporting the irradiating elements and the detecting elements in such a manner that the irradiating elements and the detecting elements are slidable and position detecting elements for detecting the position data of the irradiating elements and the detecting means with respect to the holder.

7 Claims, 2 Drawing Sheets

APPARATUS FOR OBTAINING INFORMATION ON THE INTERIOR OF AN OBJECT

BACKGROUND OF THE INVENTION

This invention relates to an apparatus for obtaining information on the interior of an object for use in a CT (computer tomography) apparatus, and more particularly to an apparatus for applying an electromagnetic wave such as a light beam, X-rays or gamma rays or an ultrasonic wave to an object under measurement, and detect the electromagnetic wave or the ultrasonic wave affected by the interior of the object, thereby to obtain information on the interior of the object.

In a conventional apparatus for obtaining information on the interior of an object such as an organism, an electromagnetic wave source located at a certain position outside the object applies an electromagnetic wave to the object, and the electromagnetic wave affected by the interior of the object is detected at plural locations. In this case, in addition to the straightly-propagating component of the electromagnetic wave, the components scattered by the object are also positively utilized so that the relationships between the electromagnetic waves thus detected are analyzed to perform an image reconstruction, thereby to obtain information on the interior of the object. Such a conventional apparatus is disclosed in detail in Japanese unexamined published patent application No. 124443/87.

In the case of an X-ray CT apparatus, only the straightly-propagating component of the X-rays in the interior of the object under measurement is detected. In this case, the X-ray irradiating position and the X-ray detecting position are not important factors in the image reconstruction.

On the other hand, for the above-described conventional apparatus for obtaining information on the interior of an object in which the scattered components of the electromagnetic wave are positively utilized, the positions of an electromagnetic wave irradiating point and a number of electromagnetic wave detecting points are essential for the image reconstruction because boundary conditions for the image reconstruction cannot be determined if those positions are unknown and it is difficult to form a CT image. In the case where the object is an organism, no suitable means is available for detecting the positions of the electromagnetic wave irradiating position and the electromagnetic wave detecting positions because the organism is generally intricate in configuration and not rigid.

SUMMARY OF THE INVENTION

An object of the invention is to provide an apparatus for measuring the interior of an object to be measured, in which boundary conditions for an image reconstruction can be determined.

The foregoing object of the invention has been achieved by the provision of the apparatus comprising: irradiating means for applying an electromagnetic wave or ultrasonic wave to an object being measured; detecting means for detecting the electromagnetic wave or ultrasonic wave affected by the object; a holding means for supporting the irradiating means and the detecting means in such a manner that the irradiating means and the detecting means are slidable; and position detecting means for detecting the position data of the irradiating means and the detecting means with respect to the holding means.

According to this invention, an electromagnetic or ultrasonic wave is applied to an object being measured by the irradiating means and the electromagnetic or ultrasonic wave passed through and scattered by the interior of the object is detected by the detecting means, thereby to perform an image reconstruction and obtain information on the interior of the object. In order to perform the image reconstruction according to the electromagnetic or ultrasonic wave, it is essential to have the boundary conditions; i.e., the configuration data of the object. In order to meet this requirement, according to this invention, the irradiating means and the detecting means are slidably supported by the holding means and those means are brought into contact with the object under suitable pressure during measurement of the object while the position data of the irradiating means and the detecting means with respect to the holding means are detected by the position detecting means, thereby readily determing the boundary conditions.

DETAILED DESCRIPTION OF THE INVENTION

A preferred embodiment of this invention will be described with reference to the accompanying drawings.

Figure 1:
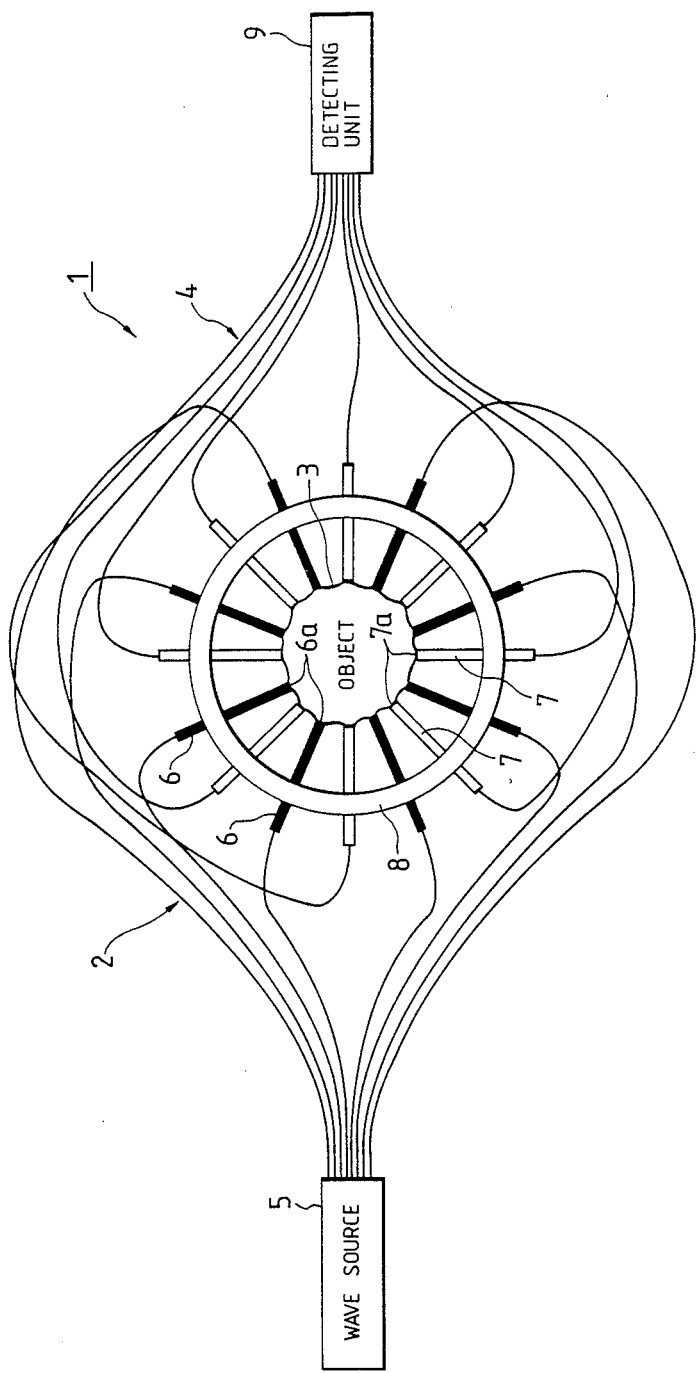
FIG. 1 is schematic diagram showing the arrangement of one example of an apparatus for obtaining information on the interior of an object according to this invention.

As shown in FIG. 1, the apparatus of the present invention comprises irradiating means 2 for applying an electromagnetic wave to an object 3 and detecting means 4 for detecting the electromagnetic waves passed through the object 3 and scattered inside the object.

The irradiating means 2 comprises a wave source 5 for outputting an electromagnetic wave, and irradiating elements 6 for guiding the output electromagnetic wave of the source 5 and applying it to the object 3. The detecting means 4 comprises detecting elements 7 for receiving electromagnetic waves from the object 3, and a detecting unit 9 for obtaining information on the interior of the object 3 on the basis of the electromagnetic waves outputted from the detecting elements 7. The irradiating elements 6 and the detecting elements 7 are supported by a holder 8 in such a manner that they are slidable relatively to the holder.

Figure 2:
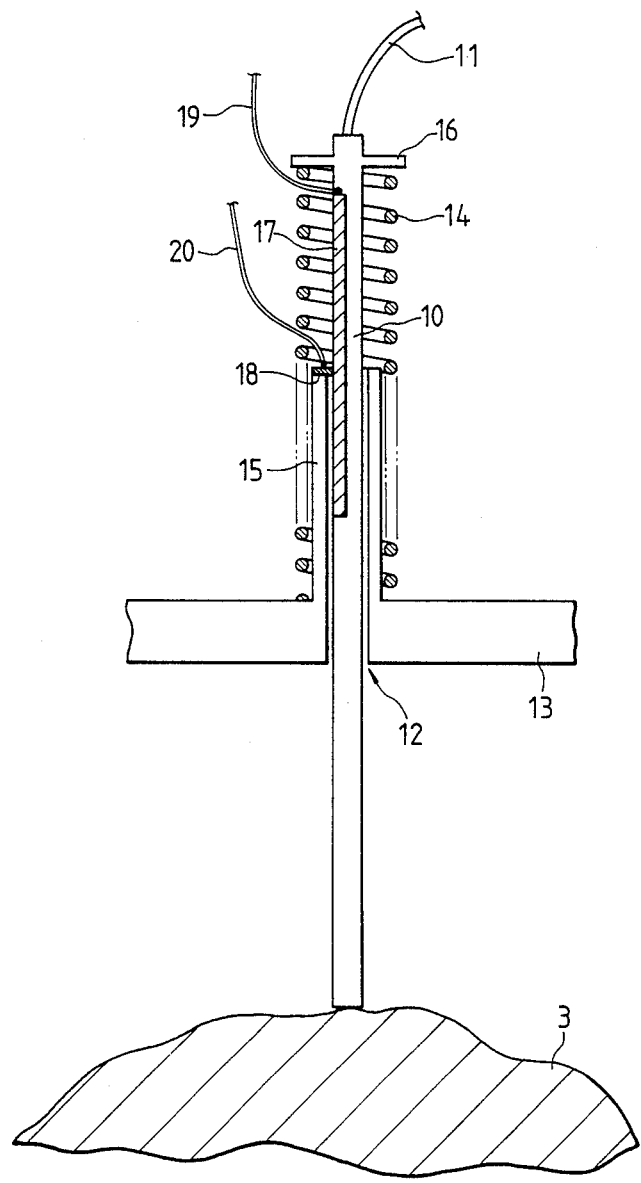
FIG. 2 is a schematic diagram showing a part of a holder in the apparatus of the invention.

FIG. 2 shows a part of the holder 8 which supports the irradiating elements 6 and the detecting elements 7. As shown in FIG. 2, the irradiating element 6 or the detecting element 7 comprises a fiber fixing cylinder 10, and a fiber 11 fixedly inserted into the cylinder 10. The holder 8 comprises a holder body 13, and springs 14 holding the irradiating elements 6 and the detecting elements 7, that is, the fiber fixing cylinders 10.

The holder body 13 may be shaped in correspondence with the configuration of an object 3 being measured. For instance, in the case where the object 3 is the man's head, the holder body 13 may be in the form of a semi-spherical helmet. The holder body 13 has annular members 15 at the positions at which the fiber fixing cylinders 10 are supported. The annular members 15 have through-holes 12, respectively. The fiber fixing cylinders 10 are slidably extended respectively through the through-holes 12 towards the object 3. The springs 14 are positioned along the annular members 15. One end of each spring 14 is secured to the holder 13 while the other end is secured to the flange 16 of the fiber fixing cylinder 10 so that the fiber fixing cylinder 10 is urged towards the object 3 and pushed against the object under a suitable pressure.

The fiber fixing cylinder 10 has a resistor 17 formed in the outer surface thereof in such a manner that the resistor 17 is extended along the axis of the cylinder 10, and the annular member 15 has a contact terminal 18, for instance, at the upper end thereof in such a manner that the contact terminal 18 is in contact with the resistor 17. A lead wire 19 is connected to a predetermined point on the resistor 17, for instance the upper end of the resistor 17, and another lead wire 20 is connected to the contact terminal 18 so that the electrical resistance between the lead wires 19 and 20 is changed as the fiber fixing cylinder 10 moves. Therefore, when the end of the fiber fixing cylinder 10 is abutted against the object 3, the position of the end of the fiber fixing cylinder 10 with respect to the holder 13; that is, the distance between the holder body 13 and the part of the object against which the end of the fiber fixing cylinder 10 abuts can be determined by the electrical resistance between the two lead wires 19 and 20.

The operation of the apparatus thus constructed will be described.

The holder 8 supporting the irradiating elements 6 and the detecting elements 7; that is, the fiber fixing cylinders 10 is mounted on an object 3 being measured. The ends of the fiber fixing cylinders 10 are so positioned that they are suitably pushed against the object by means of the springs 14, and that the electromagnetic wave from the source 5 are positively applied to the object 3 through the irradiating ends 6a of the irradiating elements 6 and the electromagnetic waves from the object 3 are positively supplied to the detecting unit 9 through the detecting ends 7a of the detecting elements 7. In this operation, data on the position of the end of each fiber fixing cylinder 10 is detected through measurement of the resistance between the lead wires 19 and 20, and is then applied, for instance, to a computer. Thus, the distances of the irradiating ends 6a of the irradiating elements 6 and the detecting ends 7a of the detecting elements 7 from the holder 8, that is, the position data thereof can be automatically obtained. In the computer, the position data are standardized in consideration of the configuration of the object 3 to thereby obtain the relative positions of the irradiating ends 6a and the detecting ends 7a.

Thus, even in the case where the object 3 is an organism which is generally intricate in configuration and is not rigid, the positions of the irradiating ends of the irradiating elements and the detecting ends of the detecting elements can be readily measured with the holder mounted on the object. Since the measurement is performed at real time, the movement of the object 3 also can be monitored by the apparatus of this invention.

In the case where the apparatus has a number of irradiating elements 6 and a number of detecting elements 7 as shown in FIG. 1, the position data of the irradiating ends 6a of the irradiating elements 6 and the detecting ends 7a of the detecting elements 7 represent the configuration data of the measurement part of the object 3. Therefore, in reconstructing an image by detecting the electromagnetic waves scattered by the object 3, the boundary conditions can be determined according to the configuration data as described above, and the CT image can be readily obtained. Especially when the object 3 is an organism which greatly scatters light, the configuration data are considerably important, for example, for determination of a physiological condition of the organism, such as the distribution of oxygen in the brain.

In the above-described embodiment, the position data of the irradiating ends and the detecting ends are detected from the variation in electrical resistance; however, the device may be so designed that the position data are obtained by other methods utilizing, for instance, electrostatic capacity or electrostatic induction. Furthermore in the above-described embodiment, the electromagnetic wave source 5 is employed; however, for instance, an ultrasonic wave source may be employed.

As described above, in the apparatus according to this invention, the position data of the irradiating means and the detecting means which are slidably supported by the holder are easily obtained, and on the basis of the position data thus detected, the boundary conditions for image reconstruction can be readily determined.

What is claimed is:

1. An apparatus for obtaining information on the interior of an object, said apparatus comprising:
   irradiating means for applying an electromagnetic wave to an object being measured;
   detecting means for detecting the electromagnetic wave passed through and scattered inside the object, said detecting means comprising a plurality of detecting elements for receiving the electromagnetic wave from the object;
   holding means for supporting said irradiating means and said detecting means in such a manner that said irradiating means and said detecting means are slidable; and
   position detecting means for detecting the position of said irradiating means and said detecting means with respect to said holding means.

2. An apparatus as claimed in claim 1, wherein said irradiating means comprises a wave source for outputting the electromagnetic wave, and irradiating elements for guiding the electromagnetic wave from said source to the object, and wherein said detecting means further comprises a detecting unit for obtaining information on the interior of the object on the basis of the electromagnetic wave from the plurality of detecting elements.

3. An apparatus as claimed in claim 2, wherein both said irradiating elements and said plurality of detecting elements comprise fiber fixing cylinders and fibers fixedly inserted into said cylinders.

4. An apparatus as claimed in claim 3, wherein said holding means comprises holder bodies and springs for holding said cylinders.

5. An apparatus as claimed in claim 4, wherein said holder bodies have annular members having through-holes respectively at the positions at which said cylinders are supported, and said cylinders are slidably extended respectively through said through-holes toward the object.

6. An apparatus as claimed in claim 5, wherein said springs are positioned along said annular members, one end of each spring being respectively secured to each of said holder bodies and the other end being respectively secured to the end portion of each of said cylinders opposite to the object so that said cylinders are urged towards the object and pushed against the object under a suitable pressure.

7. An apparatus as claimed in claim 5, wherein each of said cylinders has a resistor formed in the outer surface thereof in such a manner that said resistor is extended along the axis of said each cylinder, each of said annular members has a contact terminal in contact with said resistor, and two wires are connected with said resistor and said contact terminal respectively so that the electrical resistance between said wires is changed according to the movement of said each cylinder.

* * * * *